United States Patent [19]

Kratky et al.

[11] Patent Number: 5,139,810
[45] Date of Patent: Aug. 18, 1992

[54] FLAVORING COMPOSITION

[75] Inventors: Zdenek Kratky; Dharam V. Vadehra, both of New Milford, Conn.

[73] Assignee: Nestec S.A., Vevey, Switzerland

[21] Appl. No.: 730,026

[22] Filed: Jul. 12, 1991

Related U.S. Application Data

[60] Continuation of Ser. No. 472,309, Jan. 30, 1990, abandoned, which is a division of Ser. No. 25,224, Mar. 12, 1987, abandoned.

[51] Int. Cl.$^5$ .......................... A23L 1/22; A23L 1/23
[52] U.S. Cl. .................................. 426/580; 426/582; 426/35; 426/42; 426/650
[58] Field of Search ................ 426/35, 42, 650, 582, 426/580

[56] References Cited

U.S. PATENT DOCUMENTS

| | | |
|---|---|---|
| 1,966,460 | 7/1934 | Otting . |
| 2,169,278 | 8/1939 | Otting .................................. 426/35 |
| 2,794,743 | 6/1957 | Farnham . |
| 3,469,993 | 9/1969 | Pangier . |
| 3,975,544 | 8/1976 | Kosikowski . |
| 4,119,732 | 10/1978 | Kratochvil . |
| 4,172,900 | 10/1979 | Dooley . |
| 4,244,971 | 1/1981 | Wargel et al. . |
| 4,379,170 | 4/1983 | Hettinga et al. . |
| 4,595,594 | 6/1986 | Lee et al. . |
| 4,675,193 | 6/1987 | Boudreaux . |

FOREIGN PATENT DOCUMENTS 2008923 6/1979 United Kingdom .

*Primary Examiner*—Joseph Golian
*Attorney, Agent, or Firm*—Vogt & O'Donnell

[57] ABSTRACT

Cheese flavorant compositions of a mixture of lipolysed cream and proteolysed hard, ripened cheese are prepared from enzymatically modified heavy cream and enzymatically modified hard, ripened cheese.

9 Claims, No Drawings

FLAVORING COMPOSITION

CROSS REFERENCE TO RELATED APPLICATIONS

This application is a continuation application of application Ser. No. 07/472,309 filed Jan. 30, 1990, now abandoned, which, in turn, is a divisional application of application Ser. No. 07/025,224, filed Mar. 12, 1987.

BACKGROUND OF THE INVENTION

The present invention relates to the production of a flavouring composition more especially to the production of a flavouring composition of a hard, ripened cheese, for example, cheddar cheese.

The development of natural sharp cheddar cheese flavour profiles usually requires long and expensive ripening of cheese for a period of several months. The changes in the flavour are produced by native, added or microbial enzymes which break down the milk components such as proteins, lipids, lactose and citrate to produce the flavour components. These flavour components exist in a finely tuned balance to provide the characteristic cheddar profile. The changes occur on a continuous basis which results in the availability of mild, medium, sharp and very sharp cheddar cheeses.

Theoretically, it should be possible to take mild cheese and produce sharp cheese flavour notes by accelerated enzyme activity. However, we have found that such processes provided spikes of individual components and not necessarily the "total" profile of cheddar cheese, although this is acceptable for certain applications.

Methods are also known for producing cheese flavourants in a short time which involve the use of cultures of microorganisms. However, the use of cultures of microorganisms is accompanied by the following disadvantages:

1) Special handling techniques are required
2) Their growth in the product and the subsequent production of desirable flavour compounds is not consistent
3) Sterile techniques are required in the production of organisms for inoculation
4) Natural variation and mutation may result in the loss of production of different metabolites
5) Microorganisms are sensitive to phages which can kill them, resulting in no growth and no production of flavourants.

SUMMARY OF THE INVENTION

We have now found that certain compositions comprising cheese or heavy cream in which the lipids or the proteins were enzymatically modified provide a variety of desired cheese flavour profiles in a relatively short period of time avoiding the disadvantages of exogenous microorganisms.

Accordingly, the present invention provides a flavouring composition comprising the following components:

a) 0 to 100% lipolysed heavy cream;
b) 0 to 100% lipolysed hard, ripened cheese; and
c) 0 to 100% proteolysed hard, ripened cheese, wherein the lipolysis of components (a) and (b) is carried out by a lipase as hereinafter defined.

Component (c) may be a product prepared by treating hard, ripened cheese with either an acid or a neutral protease, or it may be a mixture containing a hard, ripened cheese treated with an acid protease and a hard, ripened cheese treated with a neutral protease.

DESCRIPTION OF PREFERRED EMBODIMENTS

By "heavy cream" in this invention we mean a cream containing at least 36% milk fat and generally from 36% to 40% by weight milk fat based on the weight of the cream. The term "heavy cream" should also be understood to include any source of milk fat appropriately blended to make an emulsion containing at least 36% by weight of milk fat.

Examples of hard, ripened cheese suitable for preparing the flavouring compositions of the present invention include Cheddar, Swiss, Colby, Monterey, Gouda, Parmesan, Brick, Muenster, Pasta filata or any mixture of two or more thereof. The cheese may be of any age (i.e., mild, medium or sharp) but is preferably mild or medium cheese.

The components (a), (b) and (c) may be used singly or mixed in appropriate proportions to obtain the desired flavour. In a mixture comprising components (a) and (b) but not component (c), very desirable flavouring compositions may be obtained when the amount of component (a) is from 5% to 80%, preferably from 10% to 40%, and especially from 20% to 30% and the amount of component (b) is from 95% to 20%, preferably from 90% to 60%, and especially from 80% to 70% by weight based on the total weight of the mixture. In a mixture comprising components (a), (b) and (c), very desirable flavouring compositions may be obtained when the amount of component (a) is from 2% to 80%, preferably from 5% to 60%, and especially from 10% to 50%, component (b) is from 5% to 80%, preferably from 10% to 60%, and especially from 20% to 50%, and component (c) is from 5% to 93%, preferably from 10% to 85% and especially from 20% to 70% by weight based on the total weight of the mixture.

The lipolysis of the heavy cream and the cheese is carried out by means of a certain type of lipase. In general, lipases are non-specific and are capable of hydrolysing a variety of fatty acid esters. However, as used in the present invention, we mean a lipase which is more specific for the hydrolysis of esters of short chain fatty acids having up to 12 carbon atoms and has substantially no activity on esters of fatty acids having more than 12 carbon atoms. For example, pregastric lipase such as that obtained from the root of the tongue of the calf is an especially desirable lipase in the present invention and it preferably hydrolyses tributyrin ($C_4$), tricaproin ($C_6$), the activity decreases to 58% for $C_8$, 49% for $C_{10}$ and only 13% for $C_{12}$ acids while it has little or no activity on trimyristin, tripalmitin or tristearin. Lipases obtained from other sources having the same or similar specificity may also be used, e.g., salivary glands.

The lipolysed heavy cream may be obtained by modification of the heavy cream by the action of a lipase which is preferably pregastric lipase. This process may, for instance, involve mixing the lipase, salt and water with the heavy cream, and incubating at a temperature from 25° C. to 40° C. for a period of from 12 to 30 hours. The amount of lipase added may be from 0.5% to 2.5% by weight (10 to 50 units of activity), and preferably from 1.0% to 2.0% by weight, (20 to 40 units of activity), the amount of the salt added may be from 0.25% to 2.0% and preferably from 0.5% to 1.0% by weight, while the amount of water added may be from 1% to 15%, and preferably from 2.5% to 7.5% by weight, all based on the weight of the heavy cream starting material.

The lipolysed hard, ripened cheese may be obtained by mixing water, salt and a lipase which is preferably pregastric lipase with the cheese, homogenising the mixture and incubating at a temperature from 25° C. to 40° C. for a period of from 1 to 4 days. The amount of water may be from 5% to 30% and preferably from 10% to 25% by weight, the amount of salt may be from 0.25% to 2.0% and preferably from 0.5% to 1.5% by weight, and the amount of lipase may be from 0.01% to 2.5% by weight and preferably from 1.0% to 2.0% by weight, all based on the weight of the hard, ripened cheese starting material.

The neutral protease treated hard, ripened cheese may be obtained by mixing hard, ripened cheese with water and a neutral protease, i.e., having optimum activity around pH 7, and then homogenising the mixture and incubating at a temperature from 25° C. to 40° C. for a period from 12 to 30 hours. The amount of neutral protease may be from 0.01% to 1.0% by weight (3000 to 60000 units) preferably from 0.1% to 0.5% by weight (6000 to 30000 units) and the amount of water may be from 5% to 35% by weight, preferably from 15% to 25% by weight, based on the weight of the hard, ripened cheese starting material. The acid protease treated hard, ripened cheese may be obtained by mixing hard, ripened cheese with water, adjusting the pH to a value from 3 to 4 and mixing with acid stable protease, i.e., having optimum activity around pH 3–4, and incubating the mixture at a temperature from 25° C. to 40° C. for a period of from 1 to 24 hours, preferably from 3 to 12 hours. The amount of water may be from 5% to 35% by weight, preferably from 15% to 25% by weight, and the amount of acid protease may be from 0.01% to 1.0% by weight, preferably from 0.1% to 0.5% by weight, based on the weight of the hard, ripened cheese starting material.

In the foregoing description, the units of activity indicated for the enzymes are the International Units, there being a specific definition of 1 International Unit for each enzyme.

The flavouring compositions of the present invention may, if desired, be homogenised with food grade acidulants such as lactic acid or acetic acid to give a product which generally is finally pasteurised, for example, at a temperature from 60° C. to 82.5° C. for a period of time from 30 minutes to 30 seconds. It should be understood that when the flavouring composition contains two or more of the components (a), (b) and (c), these components are first mixed in the desired proportions before pasteurisation.

The flavouring compositions of the present invention provide a variety of cheese flavour profiles without the addition of other additives or ingredients, thus keeping the flavour as "natural" as possible.

The following Examples further illustrate the present invention.

EXAMPLES

Example 1

Preparation of component (a)

Lipolysed heavy cream was prepared by adding 0.8 g of salt, 5.0 g of water and 1.5 g of pregastric lipase (derived from the root of the tongue of a calf) to 100 g of heavy cream having a milk fat content of 36% and incubating at 38° C. for 16 hours.

Preparation of component (b)

Lipolysed mild cheddar cheese was prepared by adding 20 g water, 0.8 g salt and 1.5 g pregastric lipase (derived from the root of the tongue of a calf) to 100 g of mild cheddar cheese. The mixture was homogenised and incubated at 38° C. for 3 days.

Preparation of component (c)

Mild cheddar cheese proteolysed by neutral protease was prepared by mixing 100 g of mild cheddar cheese with 20 g water and 0.2 g of a neutral protease, homogenising the mixture and incubating at 38° C. for 16 hours.

The three components (a), (b) and (c) were mixed in a mixer in a ratio of 33 g lipolysed heavy cream, 33 g lipolysed mild cheddar cheese and 33 g neutral proteolysed mild cheddar cheese. The mixture was homogenised, mixed with 1.0 g lactic acid and 1.25 g acetic acid to give a paste-like product which was then pasteurised at 65° C. for 30 minutes before being refrigerated at 4° C.

The product had an excellent cheddar cheese flavour and had a long shelf-life at 4° C.

Example 2

Components (a) and (b) were prepared by the method of Example 1 and mixed in a ratio of 25 g lipolysed heavy cream and 75 g lipolysed mild cheddar cheese. The mixture was homogenised and then pasteurised before being refrigerated at 4° C. The product had an excellent cheddar cheese flavour.

Example 3

Components (a) and (c) were prepared in a similar manner to that described in Example 1 and mixed in a ratio of 25 parts of component (a) and 75 parts of component (c). The mixture was homogenised and then pasteurised in a high shear mixer before being stored at 4° C.

I claim:

1. A flavoring composition product comprising a mixture of:
    a lipolysed cream cheese product prepared by mixing heavy cream with water, salt and a lipase specific for hydrolyzing fatting acids having up to 12 carbon atoms and incubating the mixture at a temperature of from 25° C. to 40° C. for from 12 hours to 30 hours; and
    at least one proteolysed cheese selected from a group consisting of a cheese prepared by:
    (a) mixing hard, ripened cheese with water and a neutral protease, homogenizing the mixture and then incubating the homogenized mixture at a temperature of from 25° C. to 40° C. for a period of from 12 hours to 30 hours for preparing a first proteolysed cheese product;
    (b) mixing hard, ripened cheese with water, adjusting the pH of the mixture to a pH of from 3 to 4, adding an acid stable protease to the pH adjusted mixture and then incubating that mixture at a temperature of from 25° C. to 40° C. for a period of from 1 day to 4 days for preparing a second proteolysed cheese product; and
    (c) mixing the first and second proteolysed cheese products for forming a third proteolysed cheese product.

2. A flavoring composition product according to claim 1 wherein the lipase is in an amount of from 0.5% to 2.5% by weight based upon the weight of the heavy cream, the salt is in an amount of from 0.25% to 2.0% by weight based upon the weight of the heavy cream and the water is in an amount of from 1% to 15% by weight based upon the weight of the heavy cream.

3. A flavoring composition product according to claim 1 wherein the heavy cream contains at least 36% milk fat and the lipase is selected from a group consisting of pregastric lipase and lipase obtained from salivary glands.

4. A flavoring composition product according to claim 1 or 2 wherein the neutral protease is in an amount of from 0.01% to 1% by weight based upon the weight of the hard, ripened cheese and the water is in an amount of from 5% to 35% by weight of the hard, ripened cheese.

5. A flavoring composition product according to claim 1 or 2 wherein the acid protease is in an amount of from 0.01% to 1% based upon the weight of the hard, ripened cheese and the water is in an amount of from 5% to 35% by weight of the hard, ripened cheese.

6. A flavoring composition product according to claim 1 wherein the hard, ripened cheese is selected from a group consisting of a mild cheese and a medium cheese.

7. A flavoring composition product according to claim 1 comprised of the lipolysed cream cheese product and the first proteolysed cheese product.

8. A flavoring composition product according to claim 1 or 7 further comprising a food grade acidulent.

9. A flavoring composition product according to claim 1 or 7 wherein the flavoring composition product is pasteurized.

* * * * *